United States Patent
Mizoe (10) Patent No.: US 11,496,823 B2
(45) Date of Patent: Nov. 8, 2022

(54) EARPIECE

(71) Applicant: SEKISUI POLYMATECH CO., LTD., Saitama (JP)

(72) Inventor: Shinya Mizoe, Saitama (JP)

(73) Assignee: SEKISUI POLYMATECH CO., LTD., Saitama (JP)

( * ) Notice: Subject to any disclaimer, the term of this patent is extended or adjusted under 35 U.S.C. 154(b) by 0 days.

(21) Appl. No.: 17/045,410

(22) PCT Filed: Apr. 15, 2019

(86) PCT No.: PCT/JP2019/016225
§ 371 (c)(1),
(2) Date: Oct. 5, 2020

(87) PCT Pub. No.: WO2019/208315
PCT Pub. Date: Oct. 31, 2019

(65) Prior Publication Data
US 2021/0152911 A1 May 20, 2021

(30) Foreign Application Priority Data
Apr. 25, 2018 (JP) .............................. JP2018-084505

(51) Int. Cl.
*H04R 1/10* (2006.01)
*A61F 11/08* (2006.01)
*H04R 25/00* (2006.01)

(52) U.S. Cl.
CPC ............ *H04R 1/1016* (2013.01); *A61F 11/08* (2013.01); *H04R 1/1058* (2013.01); *H04R 25/658* (2013.01)

(58) Field of Classification Search
CPC . H04R 1/1016; H04R 25/652; H04R 2225/77
See application file for complete search history.

(56) References Cited

U.S. PATENT DOCUMENTS

| 4,461,290 | A | * | 7/1984 | Gardner, Jr. | ............ | A61F 11/12 |
| | | | | | | 128/866 |
| 5,917,918 | A | * | 6/1999 | Callahan | .............. | H04R 1/1016 |
| | | | | | | 381/67 |

(Continued)

FOREIGN PATENT DOCUMENTS

| CN | 103781012 A | 5/2014 |
| GB | 2559247 A | 8/2018 |

(Continued)

OTHER PUBLICATIONS

Paar, Anton, "PNR 12: Consistency of White Petrolatum (US Pharmacopeia)", Oct. 10, 2016, The Engineer, Retrieved from the Internet: < URL: https://s3-eu-central-1.amazonaws.com/centaur-wp/theengineer/prod/content/uploads/2016/10/10115523/Pharmacopoeia-US_Petrolatum.pd> (Year: 2016).*

(Continued)

*Primary Examiner* — Ryan Robinson
(74) *Attorney, Agent, or Firm* — Cermak Nakajima & McGowan LLP; Tomoko Nakajima (57) ABSTRACT

An earpiece is provided. The earpiece can deform flexibly so as to follow the earhole when in use, and the earpiece can be manufactured easily. An earpiece includes an earpiece body and a filler filled in the earpiece body. The earpiece body has a container-like base member formed of a rubber-like elastic diaphragm that is shaped like a container and has an opening portion. The earpiece body also has a lid member that seals the opening portion liquid-tightly. The filler is flowable at room temperature.

12 Claims, 7 Drawing Sheets

(56) References Cited

U.S. PATENT DOCUMENTS

| | | | | |
|---|---|---|---|---|
| 6,022,311 | A * | 2/2000 | Juneau | H04R 25/652 600/25 |
| 6,473,512 | B1 * | 10/2002 | Juneau | C07D 493/10 381/328 |
| 6,513,621 | B1 * | 2/2003 | Deslauriers | H04R 1/1016 128/865 |
| 7,162,039 | B1 * | 1/2007 | Callahan | A61B 7/02 381/374 |
| 7,227,968 | B2 * | 6/2007 | van Halteren | H04R 25/656 381/328 |
| 8,160,288 | B2 * | 4/2012 | Axelsson | H04R 1/1016 381/380 |
| 8,548,181 | B2 * | 10/2013 | Kraemer | H04R 25/652 381/322 |
| 8,897,458 | B2 * | 11/2014 | Parkins | A61F 11/08 381/72 |
| 9,313,568 | B2 * | 4/2016 | Basseas | H04L 61/2514 |
| 10,785,552 | B2 * | 9/2020 | Estabrook | H04R 1/1016 |
| 11,012,770 | B2 * | 5/2021 | Hatfield | H04R 1/1016 |
| 2009/0071487 | A1 * | 3/2009 | Keady | H04R 1/1016 128/864 |
| 2013/0101147 | A1 | 4/2013 | Kraemer | |
| 2014/0166389 | A1 | 6/2014 | Young-Mun | |
| 2015/0150728 | A1 * | 6/2015 | Duvall | H04R 25/656 128/865 |
| 2018/0160210 | A1 * | 6/2018 | Begusch | H04R 1/1016 |
| 2019/0208302 | A1 * | 7/2019 | Monti | H04R 1/1016 |
| 2020/0359122 | A1 * | 11/2020 | Casali | H04R 25/656 |
| 2020/0374615 | A1 * | 11/2020 | Anderson | A61B 5/055 |
| 2021/0152924 | A1 * | 5/2021 | Keady | H04R 1/1058 |

FOREIGN PATENT DOCUMENTS

| | | |
|---|---|---|
| JP | 52-80828 A | 7/1977 |
| JP | 3096024 U | 8/2003 |
| JP | 2004-208865 A | 7/2004 |
| JP | 2011-139180 A | 7/2011 |
| JP | 2014-087054 A | 5/2014 |
| JP | 3215127 U | 2/2018 |

OTHER PUBLICATIONS

International Search Report for PCT Patent App. No. PCT/JP2019/016225 (dated Jul. 2, 2019).

* cited by examiner

EARPIECE

This application is a national phase entry under 35 U.S.C. § 371 of PCT Patent Application No. PCT/JP2019/016225, filed on Apr. 15, 2019, which claims priority under 35 U.S.C. § 119 to Japanese Patent Application No. 2018-084505, filed Apr. 25, 2018, both of which are incorporated by reference.

TECHNICAL FIELD

The present invention relates to an earpiece that serves as an earhole-insertion member for an earphone, an earplug, a hearing aid, or the like.

BACKGROUND ART

An earpiece is a member to be inserted in an earhole of a user. Various types of earpieces are known. For example, Japanese Unexamined Patent Application Publication No. 2004-208865 (PTL 1) discloses an earplug that can be removed easily and is excellent in soundproofing and waterproofing. The earplug includes a main body made of a material having plasticity, and the entire main body is covered with a plastic film. In addition, Japanese Registered Utility Model No. 3096024 (PTL 2) discloses an ear tip for a stethoscope. The ear tip is formed flexibly so as to fit the shape of the ear and that gives a comfortable ear-fit feeling. A soft texture is provided due to a liquid or air being filled inside the peripheral walls of an ear insertion portion of the ear tip.

CITATION LIST

Patent Literature

PTL 1: Japanese Unexamined Patent Application Publication No. 2004-208865
PTL 2: Japanese Registered Utility Model No. 3096024

SUMMARY OF INVENTION

Technical Problem

The earplug according to Japanese Unexamined Patent Application Publication No. 2004-208865 (PTL 1) uses the plastic film that covers the outer surface of the earplug. In general, plastic films are bendable but are not stretchable. Accordingly, it is difficult to deform the plastic film so as to come into close contact with the inner surface of the earhole. Regarding the ear tip according to Japanese Registered Utility Model No. 3096024 (PTL 2), it is difficult to form a hollow cavity inside a portion to be inserted into the ear. It is also difficult to inject a liquid into the cavity.

The present invention is made with the above known arts as background. An object of the present invention is to provide an earpiece that can deform flexibly so as to fit an earhole when in use. Another object of the present invention is to provide the earpiece that can be manufactured easily.

Solution to Problem

To achieve above objects, an earpiece according to the present invention is configured as follows. The earpiece includes an earpiece body and a filler filled in the earpiece body. The earpiece body has a container-like base member formed of a rubber-like elastic diaphragm that is shaped like a container and has an opening portion. The earpiece body also has a lid member that seals the opening portion liquid-tightly. The filler is flowable at room temperature.

The earpiece body has the container-like base member formed of the rubber-like elastic diaphragm that is shaped like a container and has the opening portion, and the earpiece body also has the lid member that seals the opening portion liquid-tightly. Accordingly, the earpiece body can be manufactured easily by fixing the lid member to the container-like base member. The container-like base member is formed of the rubber-like elastic diaphragm, and the filler filled in the earpiece body is flowable at room temperature. Accordingly, the earpiece can deform flexibly so as to follow the shape of the earhole when in use.

The container-like base member may have a hollow and annular shape, and the lid member may have a tabular and annular shape. Due to the container-like base member having the hollow and annular shape, the earpiece can have a through hole at the center thereof, and the through hole can serve as a sound passage. Accordingly, the earpiece can be applied advantageously to an earphone. The earpiece body is configured to have the container-like base member having the hollow and annular shape and the lid member having the tabular and annular shape. The earpiece can be made to have a simple configuration of a two-piece structure.

The earpiece body may have a rigid cylinder member at least formed in the container-like base member or at the inner peripheral portion of the lid member. The rigid cylinder member at least formed in the container-like base member or at the inner peripheral portion of the lid member can retain the shape of the sound passage.

The filler may be at least any one of a liquid substance, a viscous fluid, and a gel-like substance that are made of at least any one of paraffin, liquid paraffin, silicone oil, silicone grease, silicone gel, and urethane gel. With this configuration, the filler is harmless to human body in case of filler leakage. In addition, the filler can deform and flow at room temperature so as to follow the shape of the earhole and thereby bring the container-like base member into close contact with the inner surface of the earhole.

The rubber-like elastic diaphragm may be made of at least any one of silicone rubber, butyl rubber, and urethane rubber that have a hardness of 5 to 30 in terms of JIS A-hardness. With this configuration, the rubber-like elastic diaphragm can deform so as to follow the inner surface of the earhole, bringing the container-like base member into close contact therewith.

The container-like base member may have a wide fixation end that is formed at the opening portion by increasing a thickness of the rubber-like elastic diaphragm from a portion below the opening portion toward the opening portion. The wide fixation end can provide a wide fixation area to be fixed to the lid member, which increases the strength of fixation of the lid member to the container-like base member. This can provide an earpiece of which the filler does not leak easily.

The earpiece body may have an accommodation region for the filler inside the container-like base member that is sealed by the lid member, and the filler may occupy 50 to 100 volume percent of the accommodation region. With this configuration, the flexibility of the filler can be balanced appropriately with the rubber-like elastic diaphragm of the container-like base member, which can give a comfortable ear-fit feeling while the earpiece is in close contact with the ear.

The rubber-like elastic diaphragm may have an infiltration prevention coating of low permeability for the filler or air that is formed on an inner or outer surface of the rubber-like elastic diaphragm. The rubber-like elastic diaphragm having the infiltration prevention coating can prevent the filler from leaking and air from permeating the earpiece body.

The container-like base member may have an end portion positioned on a side that is closer to an end to be inserted into an auricle and a swelling portion that bulges relative to the end portion in a radial direction of the container-like base member. With this configuration, the end portion positioned on the side closer to the end to be inserted in the auricle is formed to be thinner than the swelling portion. This enables the end portion to be disposed in the ear so as to be spaced from the wall of the earhole, which enables the end portion to be inserted deeper into the ear while reducing an uncomfortable ear-fit feeling. In addition, since the swelling portion is thicker than the end portion, the swelling portion of the earpiece can be reliably brought into contact with the inner surface of the auricle. Moreover, when the earpiece is inserted into the auricle, the large-diameter swelling portion can be held securely by fingers, which facilitates insertion of the earpiece into the auricle.

The container-like base member may have an ear-insertion-side end portion to be inserted into the auricle, and the ear-insertion-side end portion may have a curved shape. The curved shape guides the ear-insertion-side end portion and thereby facilitates insertion of the earpiece into the auricle. In the container-like base member configured to have a hollow and annular shape, the ear-insertion-side end portion may have a curved outer portion formed at an outer wall of the container-like base member and a curved inner portion formed at an inner wall of the container-like base member. The curved outer portion eliminates an angled corner portion. Accordingly, when inserted into the auricle, the curved outer portion can guide the earpiece and does not irritate the auricle, as may occur in the case of the angled corner portion. Because of the curved inner portion, the end of the central through hole of the hollow and annular container-like base member opens like a trumpet. The sound passing the through hole can be output so as to spread along the curved inner portion.

The container-like base member may have a fingerhold that protrudes outward relative to the lid member. Accordingly, when the earpiece is removed from the auricle, for example, the earpiece can be pulled out easily with fingers holding the fingerhold. In addition, after the earpiece is removed from the auricle, the earpiece can be held at the fingerhold that is not inserted into the auricle and stays outside. This is convenient because those who feel reluctant from a hygienic point of view to hold a portion to be in contact with the earhole can hold the fingerhold without concern.

Advantageous Effects of Invention

The earpiece according to the present invention can deform flexibly so as to follow the earhole when in use. In addition, the earpiece according to the present invention can be manufactured easily.

BRIEF DESCRIPTION OF DRAWINGS

FIG. 1 Segment 1A and Segment 1B of FIG. 1 are bottom and front views, respectively, illustrating an earpiece according to a first embodiment of the present invention.

DESCRIPTION OF EMBODIMENTS

The present invention will be described in detail with reference to embodiments. Note that the descriptions of the same material, composition, production method, advantageous effects, or the like will not be repeated for each embodiment below.

Figure 1A:
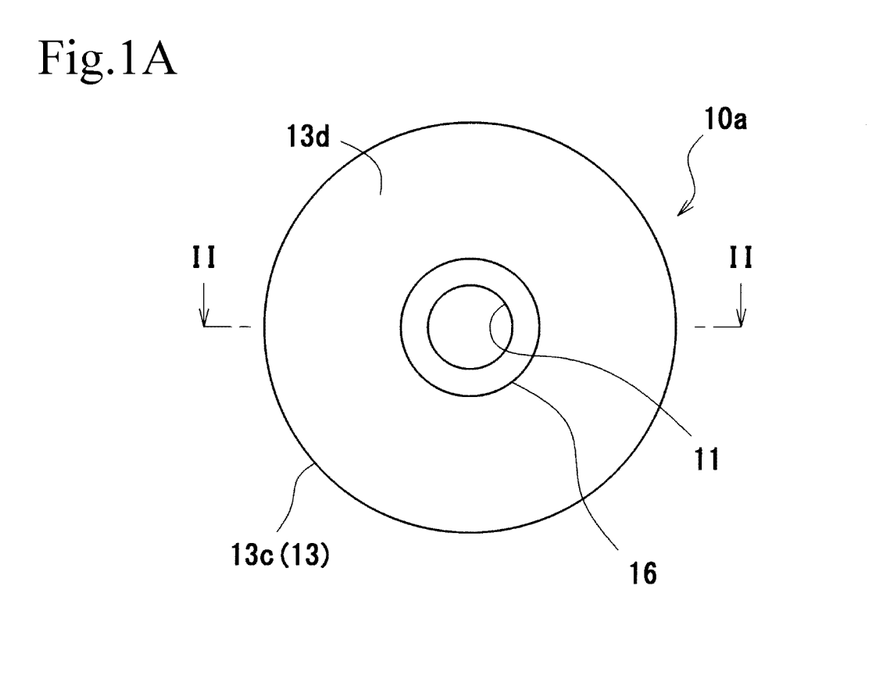
Figure 1B:
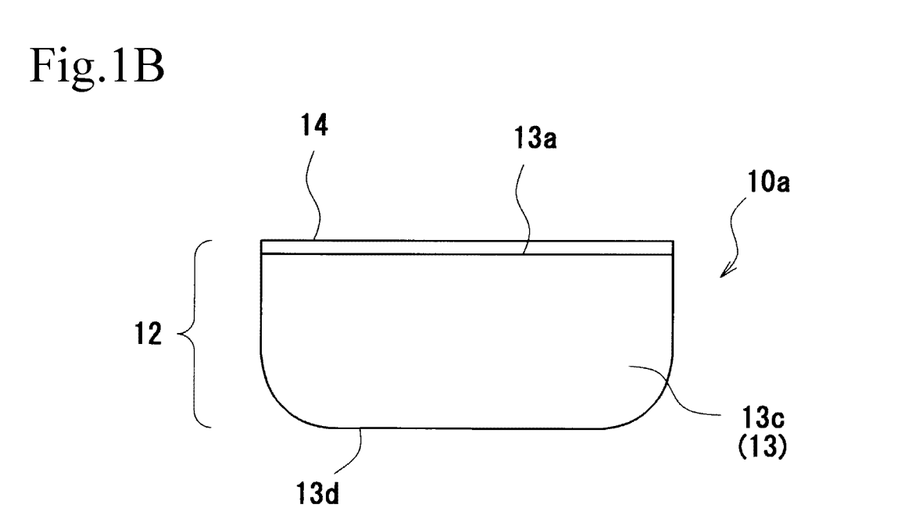
Figure 2:
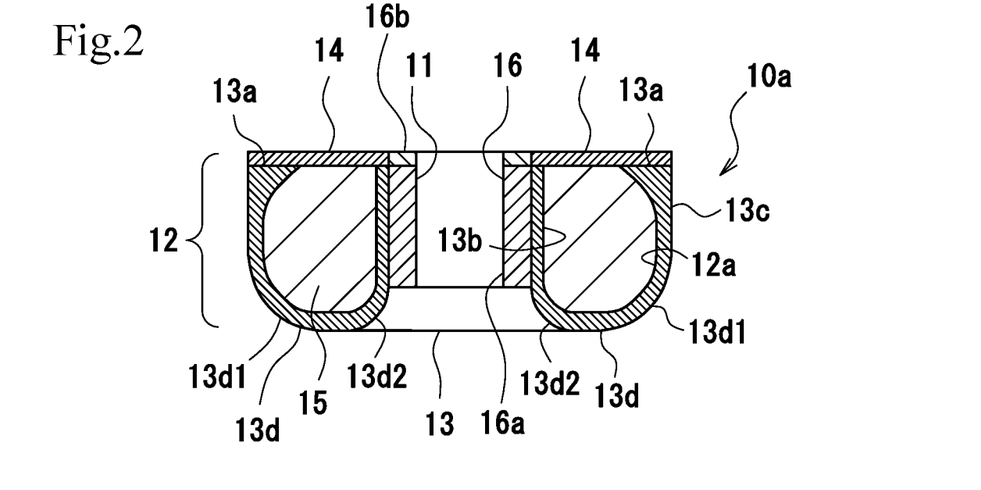
FIG. 2 is a cross-section of the earpiece taken along line II-II in FIG. 1A.
Figure 3:
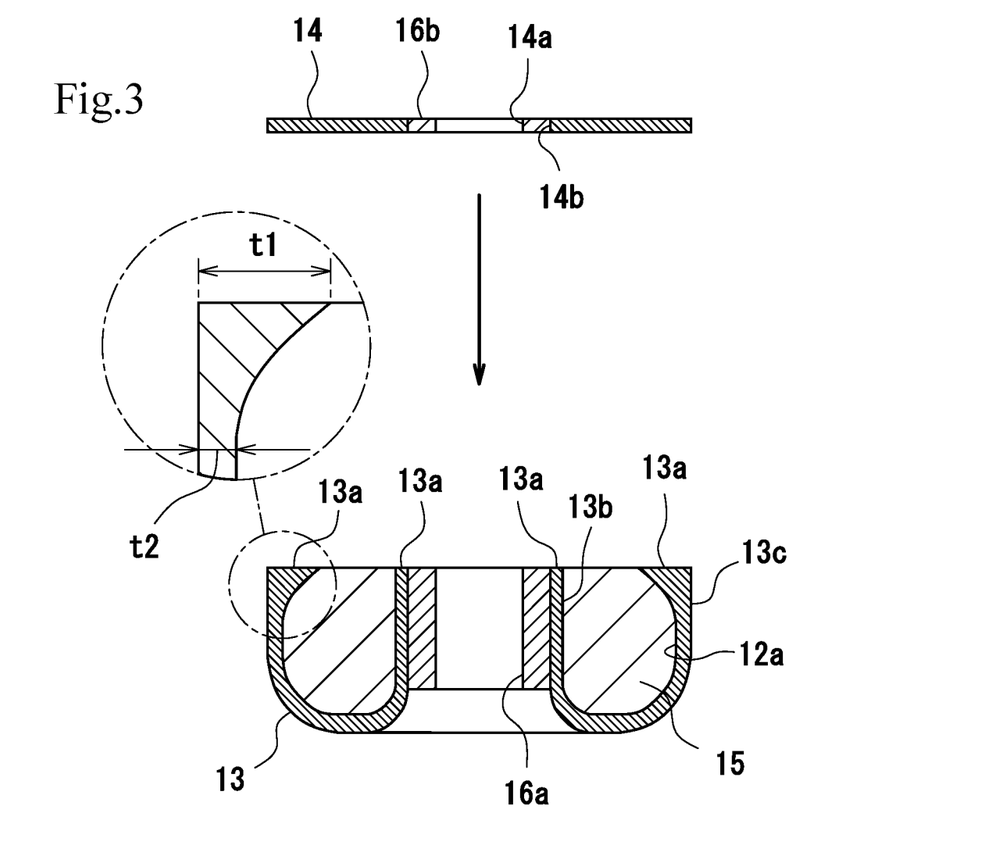
FIG. 3 is a diagram for explanation of a manufacturing method of the earpiece of FIG. 1.

First Embodiment (FIGS. 1 to 3)

An earpiece 10a is formed of an earpiece body 12 that includes a container-like base member 13 and a lid member 14, a filler 15 sealed in the earpiece body 12, and a rigid cylinder member 16 that is disposed at an inner wall 13b, which serves as an "inner peripheral portion" of the container-like base member 13.

The container-like base member 13 is formed of a rubber-like elastic diaphragm as a hollow container having an opening portion 13a. The opening portion 13a is formed annularly. An annularly shaped lid member 14 is fixed to the opening portion 13a to form the earpiece body 12, which will be described in detail later. As illustrated in FIG. 1A, the earpiece 10a according to the present embodiment is shaped like a doughnut as viewed in plan and has a through hole 11 formed at the center thereof. In the front view of the earpiece 10a in FIG. 1B, the side of the earpiece 10a at the lid member 14 has right-angled corners, whereas the side opposite to the lid member 14 has round corners.

An end portion of the container-like base member 13 that is located opposite to the lid member 14 has an ear-insertion-side end portion 13d to be inserted into an auricle. The ear-insertion-side end portion 13d has a curved outer portion 13d1 that is curved from an outer wall 13c of the container-like base member 13 to the end thereof. The ear-insertion-side end portion 13*d* also has a curved inner portion 13*d*2 that is curved from the inner wall 13*b* of the container-like base member 13 to the end thereof. The curved outer portion 13*d*1 enables the earpiece 10*a* to enter an earhole easily. Due to the curved inner portion 13*d*2 being provided, the through hole 11 expands toward the outside like a trumpet, which enables sound passing through the through hole 11 to readily spread in the ear. In addition, the curved outer portion 13*d*1 and the curved inner portion 13*d*2 formed at the end of the ear-insertion-side end portion 13*d* can advantageously suppress trapping of bubbles when the filler 15 is poured thereinto during manufacturing the earpiece 10*a*. Note that the end of the container-like base member 13 located opposite to the lid member 14 may be formed, for example, into a round shape like a doughnut, into a bellows having a narrow portion, or into a shape tapered toward the end, as well as into the shape illustrated in FIG. 2.

The opening portions 13*a*, which provide fixation surfaces or "fixation ends" to be fixed to the lid member 14, are preferably aligned on a single plane to facilitate adhesion of the opening portions 13*a* to the lid member 14. However, the opening portion 13*a* of inner wall 13*b* and the opening portion 13*a* of outer wall 13*c* of the container-like base member 13 may be formed so as to have different heights. The rubber-like elastic diaphragm that forms the container-like base member 13 has a small vertical horizontal cross-sectional area. If the cross-sectional area were the entire adhesion area of the opening portion 13*a* for adhesion to the lid member 14, the adhesion area would not be large enough to provide a sufficient fixation strength. Accordingly, the thickness of the rubber-like elastic diaphragm is gradually increased toward the opening portion 13*a* in such a manner that the length of the opening portion 13*a* measured in a direction parallel to the radial direction of the lid member 14 (i.e., length t1 in FIG. 3) is longer than the corresponding length of an average thickness portion of the rubber-like elastic diaphragm that forms the container-like base member 13, in other words, the thickness of outer wall 13*c* of the container-like base member 13 at an intermediate position (i.e., length t2 in FIG. 3). In FIG. 3, the top end of the inner wall 13*b* of the earpiece 10*a* is not made wide. It is preferable, however, that the opening portion 13*a* at the top end of the inner wall 13*b* be made wide in a manner similar to the opening portion 13*a* at the top end of the outer wall 13*c* from a viewpoint of increasing the fixation area between the opening portion 13*a* and the lid member 14 and thereby increasing the fixation strength.

The container-like base member 13 preferably has flexibility and stretchability so as to be able to deform freely. Accordingly, the container-like base member 13 is formed of a rubber-like elastic diaphragm. For example, the rubber-like elastic member that forms the container-like base member 13 may be made of a thermoplastic elastomer or a thermosetting rubber. For example, the thermoplastic elastomer may be styrenic elastomer, olefinic elastomer, polyester elastomer, polyurethane elastomer, polyamide elastomer, or the like. The thermosetting rubber may be styrene rubber, butadiene rubber, isoprene rubber, nitrile rubber, butyl rubber, chloroprene rubber, ethylene-propylene rubber, silicone rubber, acrylic rubber, urethane rubber, fluoro rubber, or the like. The material preferably has such properties that the material does not readily absorb the filler 15 and air does not readily permeate the material. It is preferable to use silicone rubber because it does not leave a permanent strain easily after compression or elongation and can be made less rigid.

The rubber-like elastic member that forms the container-like base member 13 has preferably a low hardness value, for example, a rubber hardness of about 5 to 30 and, more preferably, 10 to 20 in terms of JIS A-hardness. The rubber-like elastic member preferably exhibits an elongation of 200% or more. If the hardness is less than 5 of A-hardness, the strength of the rubber-like elastic diaphragm may be too low, and the rubber-like elastic diaphragm may be vulnerable to breakage. If the hardness is more than 30 of A-hardness, the rubber-like elastic diaphragm may not provide a soft texture. If the elongation of the rubber-like elastic member is less than 200%, the earpiece 10*a* may be vulnerable to breakage when the earpiece 10*a* is deformed.

The thickness of rubber-like elastic diaphragm of the container-like base member 13 is preferably in the range of 0.1 mm to 2 mm. If the thickness is less than 0.1 mm, the rubber-like elastic diaphragm may be vulnerable to breakage. If the thickness is more than 2 mm, the filler 15 filled inside may not exhibit its advantageous properties through the rubber-like elastic diaphragm.

The lid member 14 is a member for closing the opening portions 13*a* of the container-like base member 13 so as to seal the filler 15 therein. The lid member 14 is preferably formed into a tabular shape from a viewpoint of easy manufacture. In the present embodiment, the lid member 14 is formed into a doughnut-like plate having a hole 14*a* that matches the inner wall 13*b* of the container-like base member 13. In the case in which the opening portion 13*a* of the inner wall 13*b* and the opening portion 13*a* of the outer wall 13*c* of the container-like base member 13 are formed so as to have different heights, the lid member 14 may be formed into a shape with the outer and inner peripheries thereof having different heights so as to match the opening portions 13*a*.

The lid member 14 may be made of a material similar to that of the container-like base member 13. In other words, the container-like base member 13 may be made of a silicone rubber, and the lid member 14 may be made of the same silicone rubber. Alternatively, the container-like base member 13 may be made of a type of silicone rubber, and the lid member 14 may be made of a different type of silicone rubber. Moreover, the container-like base member 13 may be made of a silicone rubber, and the lid member 14 may be made of a butyl rubber. Using similar materials is preferable because it is easier to select an adhesive adherable to both container-like base member 13 and lid member 14. Using similar materials is preferable also because the earpiece 10*a* as a whole can provide a uniform texture.

The lid member 14 may be made of a material different from that of the container-like base member 13. For example, the lid member 14 may be formed of a resin film or a resin plate, whereas the container-like base member 13 is formed of the rubber-like elastic diaphragm. The resin film is preferable because the resin film forms a light-weight earpiece that can reduce a load on the ear and also reduce the manufacturing cost.

The rigid cylinder member 16 is a cylindrically shaped member that is formed of a rigid material and fixed to the inner peripheral surfaces of the container-like base member 13 and the lid member 14. The rigid cylinder member 16 includes a base-side cylinder portion 16*a* that is fixed to the inner wall 13*b* of the container-like base member 13 and a lid-side cylinder portion 16*b* that is fixed to the inner peripheral surface of the lid member 14. The base-side cylinder portion 16*a* and the lid-side cylinder portion 16*b* are fixed to each other by fixing the lid member 14 to the container-like base member 13, which thereby forms the rigid cylinder member 16. The base-side cylinder portion 16a is shaped like a cylinder. The entire outer peripheral surface of the base-side cylinder portion 16a is fixed to the inner wall 13b of the container-like base member 13. The lid-side cylinder portion 16b is shaped like a disk. The entire outer peripheral surface thereof is fixed to the inner peripheral portion of the rubber-like elastic diaphragm that forms the lid member 14. The rigid cylinder member 16 is made of a material more rigid than that of the container-like base member 13. This can prevent excessive deformation of the container-like base member 13 and thereby prevent the through hole 11 serving as the sound passage from being flattened. In addition, the rigid cylinder member 16 made of the rigid material reduces absorption of sound and facilitates transmission of sound into the ear.

The end of the rigid cylinder member 16 located opposite to the lid member 14 is positioned inside the end of the container-like base member 13 (i.e., the ear-insertion-side end portion 13d), which thereby prevents the rigid cylinder member 16 from coming into contact with the ear and also allows the end of the container-like base member 13 to deform freely. In addition, the lid-side cylinder portion 16b, which is the end portion of the rigid cylinder member 16 at the lid member 14, is formed so as to reach an inner peripheral surface 14b of the lid member 14 formed of the rubber-like elastic diaphragm and so as to be flush with the surface of the lid member 14. In the present embodiment, the lid-side cylinder portion 16b, which is part of the rigid cylinder member 16, is provided at the inner peripheral surface 14b of the lid member 14, which thereby eliminates the necessity of increasing the thickness of the opening portion 13a of inner wall 13b of the container-like base member 13. The base-side cylinder portion 16a disposed in the container-like base member 13 and the lid-side cylinder portion 16b disposed in the lid member 14 are made of the same material, which thereby increases the adhesive strength therebetween. This compensates an insufficient adhesive strength between the lid member 14 and the inner wall 13b of the container-like base member 13. Moreover, this can enlarge the opening of the container-like base member 13 and facilitate injection of the filler 15 into the container-like base member 13 in manufacturing.

The rigid cylinder member 16 serves to retain the shape of the inner wall 13b and also retain the shape of opening of the container-like base member 13. In this regard, the container-like base member 13 is devised to facilitate injection of the filler 15. The lid-side cylinder portion 16b of the rigid cylinder member 16 functions as a "fixation end" for fixation of the lid member 14. The lid member 14 including the lid-side cylinder portion 16b is configured to be fixed to the container-like base member 13 so as to seamlessly seal the top end of base-side cylinder portion 16a of the rigid cylinder member 16 and the opening portion 13a of the container-like base member 13. Accordingly, liquid leakage can be reliably prevented.

The rigid cylinder member 16 may be preferably formed of a hard resin that is excellent in terms of mechanical strength, thermal resistance, durability, accuracy of dimension, and reliability and that is light weight and has workability. The hard resin may be a thermoplastic resin, such as polypropylene resin, polyethylene resin, polyvinyl chloride resin, polystyrene resin, acrylonitrile-styrene-acrylate resin, acrylonitrile-butadiene-styrene resin, polyamide resin, polyacetal resin, polycarbonate resin, polyethylene terephthalate resin, polybutylene terephthalate resin, polyphenylene oxide resin, polyphenylene ether resin, polyphenylene sulfide resin, polyurethane resin, liquid crystalline polymer, and composite resin of these. The hard resin may be a thermosetting resin, such as epoxy resin and urethane resin. An impact-absorbing hard resin may be used to improve shock-absorbing performance.

The filler 15 may be, for example, a liquid, a viscous material, or a gel that can flow at room temperature and may be an oil-based or a water-based material. The filler 15, which is a material such as a liquid, a viscous material, or a gel flowable at room temperature, provides the earpiece with soft and flexible properties compared with a solid or foamed material made of a cross-linked polymer. This enables the earpiece to follow the shape of the ear and thereby gives a better ear-fit feeling. The filler 15 insulates the earpiece against external sounds more effectively compared with an earpiece filled with nothing. The material of the filler 15 may be, for example, paraffin, liquid paraffin, silicone grease, silicone gel, silicone oil, urethane gel, or a slime material. Among these, paraffin, liquid paraffin, or silicone oil is preferable from a viewpoint of not having a harmful effect on human body in case of spillage of the filler 15. From a viewpoint of not causing spillage easily, for example, silicone grease, silicone gel, urethane gel, or a slime material is preferable. In the present invention, "a material flowable at room temperature" means a material that is flowable or deformable at a temperature of 25° C.

In order to adjust, for example, viscosity, sound insulating properties, and vibration damping properties, an additive or a powder or the like may be added to the filler 15 insofar as such an additive does not impair the flowability of the filler 15 at room temperature. In the case of a water-based filler 15, the viscosity of the filler 15 can be adjusted by adding a thickener, a stabilizer, a gelatinizer, or a glue, such as carrageenan, sodium carboxymethylcellulose, xanthan gum, guar gum, or pectin. Other additives like an antiseptic may be added to the filler 15. A slime material made by adding borax to PVA also can be used. A fine powder, such as silica powder or a resin powder (e.g., polyethylene powder), may be added. Adding these materials can hinder sound from passing through the filler 15, which improves sound insulation or attenuation for blocking external noise from entering. For example, silicone oil containing a fine powder listed above can be used advantageously to adjust sound insulation and vibration damping properties while maintaining a high viscosity. A liquid material, such as paraffin or liquid paraffin, that contains a fine powder listed above can be also used for this purpose.

The viscosity of the filler 15 is preferably in the range of 100,000 cSt to 3,000,000 cSt. When a viscous fluid is used, the consistency of the filler 15 measured using the one-quarter cone device is preferably in the range of 100 to 800. When a gel-like material is used, the needle penetration number of the filler 15 is preferably in the range of 100 to 500. If the viscosity of the filler 15 is less than 100,000 cSt or if the consistency of the viscous fluid measured by the one-quarter cone exceeds 800 or if the needle penetration number of the gel-like material exceeds 500, the filler 15 is too fluid and thereby causes the container-like base member 13 to be more resilient, as is the case in which an accommodation region 12a for containing the filler 15 is empty. This deteriorates the ear-fit feeling. Moreover, in case of the container-like base member 13 being broken, the filler 15 flows out easily. On the other hand, if the viscosity of the filler 15 is more than 3,000,000 cSt or if the consistency of the viscous fluid measured by the one-quarter cone is less than 100 or if the needle penetration number of the gel-like material is less than 100, the filler 15 is too firm and thereby causes the container-like base member 13 to be less flexible.

This may lead to an uncomfortable ear-fit feeling. In the preferable range of the viscosity or the needle penetration number, a relatively viscous filler 15 tends to suppress an uncomfortable ear-fit feeling. The above-described results of the one-quarter cone or the needle penetration are obtained in accordance with JIS K2220.

The filler 15 is preferably a thixotropic fluid. Accordingly, the earpiece 10a can be put easily in the earhole due to the earpiece 10a being deformed and cannot be pulled out easily when in use due to the earpiece 10a retaining its shape. The thixotropic index (TI) of the filler 15 is preferably in the range of more than 1 and 5 or less. The thixotropic index of 1 or less or of more than 5 cannot fully provide advantageous effects of using the thixotropic fluid that the earpiece 10a can be put into the earhole easily due to deformation and cannot be pulled out easily due to shape retention.

Since the earpiece 10a containing the filler 15 is less resilient, the earpiece 10a is deformed and thereby put in the earhole easily, and the earpiece 10a maintains its shape when in use and does not press the earhole strongly. This makes the earpiece 10a a comfortable earpiece for use for a long time. The filler 15 filled in the earpiece can retard the elastic recovery of the rubber-like elastic material of the container-like base member 13.

The retardancy of the elastic recovery can be expressed in terms of hysteresis loss rate (in accordance with JIS K6400-2). The hysteresis loss rate indicates loss of mechanical energy in one deformation-recovery cycle and can be determined from the stress-deflection curve obtained from the compression-deflection test. The greater the hysteresis loss rate, the slower the recovery and the smaller the repulsive force after deformation. In the case of the earpiece, this means that the force pressing the earhole is weakened after the earpiece is pushed into the earhole. The hysteresis loss rate of the earpiece is preferably 25% or more. The compression-deflection test is performed at a compression rate of 10 mm/minute under the whole-surface loading condition up to 1 kgf. The hysteresis loss rate in compression and recovery is measured with a retention time of 0 second.

The filler 15 preferably occupies 50 to 95 volume percent (vol %), or more than 95 vol % to less than 100 vol %, or 100 vol %, of the accommodation region 12a that is formed inside the earpiece body 12 for accommodating the filler 15. If the amount of the filler 15 is less than 50 vol %, advantageous effects of using the filler 15 cannot be fully obtained as is the case of the accommodation region 12a being empty. If the amount of the filler 15 is more than 100 vol %, the earpiece becomes less flexible and repulsive when pressed, which gives an uncomfortable hard feeling. In the case of charging the filler 15 to the amount of 50 to 95 vol %, a considerable amount of bubbles of air or a gas is also accommodated in the earpiece body 12. In this case, characteristics of bubbles can be added to the earpiece. In the case of charging the filler 15 to the amount of more than 95 vol % and less than 100 vol %, a small amount of bubbles is accommodated in the earpiece body 12 between the filler 15 and the rubber-like elastic diaphragm, which makes the most of characteristics of the rubber-like elastic diaphragm and the filler 15. In the case of charging the filler 15 to the amount of 100 vol %, the filler 15 and the rubber-like elastic member can be integrated without being affected by the bubbles. In summary, adjusting the amount of the filler 15 gives a different ear-fit feeling.

Low-permeability infiltration prevention coating or other type of surface treatment may be performed on the inner or the outer surfaces of the container-like base member 13 and lid member 14 for the purpose of preventing the filler 15 or air from permeating or penetrating therethrough. The infiltration prevention coating may be, for example, fluorine-based coating, butyl rubber coating, or polyurethane-based coating. The surface treatment may be a water-repellent treatment or an oil-repellent treatment known in the art. In addition, silicone-based coating may be performed for the purpose of smoothing or glazing the outer surfaces.

The lid member 14 is adhered to the container-like base member 13 using an adhesive or a glue or using a method, such as welding or fusing. The adhered portion needs to exhibit flexibility after adhesion. Accordingly, when an adhesive is used, it is preferable to use an adhesive that exhibits flexibility after adhesion. In addition, when an adhesive or a glue is used, the material of the adhesive or the glue preferably prevents the filler 15 from permeating or penetrating therethrough. For example, the container-like base member 13 and the lid member 14 may be both made of a silicone rubber and be adhered to each other using a silicone-based adhesive. The material combination of this example is preferable because this example did not exhibit filler leakage after subjected to repeated flattening and recovery for 5000 times, and this example also withstood up to 100 kgf in loading test.

Next, an example of method of manufacturing the earpiece 10a will be described. FIG. 3 is a diagram illustrating the container-like base member 13 and the lid member 14 to be integrated into one body. The container-like base member 13 and the lid member 14 are formed of a rubber-like elastic member into predetermined shapes in advance. Here, the base-side cylinder portion 16a is integrated into the inner wall 13b of the container-like base member 13, and the lid-side cylinder portion 16b is also integrated into the inner peripheral surface 14b of the lid member 14. This integration can be carried out, for example, using insert molding or adhesion of a hard material member. The filler 15 is also prepared in advance.

Next, a predetermined amount of the filler 15, which is necessary to give a desired ear-fit feeling, is injected into a hollow region (accommodation region 12a) in the container-like base member 13. When a less flowable material is injected, the material may be heated to improve the fluidity. Subsequently, the lid member 14 is fixed to the opening portions 13a (i.e., "fixation ends") of the container-like base member 13 using an adhesive or a glue or welding or fusion. The lid-side cylinder portion 16b is simultaneously fixed to the base-side cylinder portion 16a using an adhesive or a glue or welding or fusion. Alternatively, the material of the lid member 14 may be placed on the container-like base member 13 that is placed in a die and may be integrated into one body by cross-linking. The earpiece 10a can be manufactured easily in such manners. The earpiece 10a obtained can be deformed so as to follow an earhole, thereby coming into close contact therewith and giving an intended ear-fit feeling. The earpiece 10a is excellent in sound insulation due to the filler 15 absorbing external sound coming in the earpiece 10a. When the earpiece 10a is used for an earphone, the undeformed rigid cylinder member 16 of the earpiece 10a allows sound to pass through without attenuating a low-pitched sound. When the earpiece 10a is fitted to the earphone, an earphone member, such as a driver unit, is to be disposed on the lid member 14.

Figure 4:
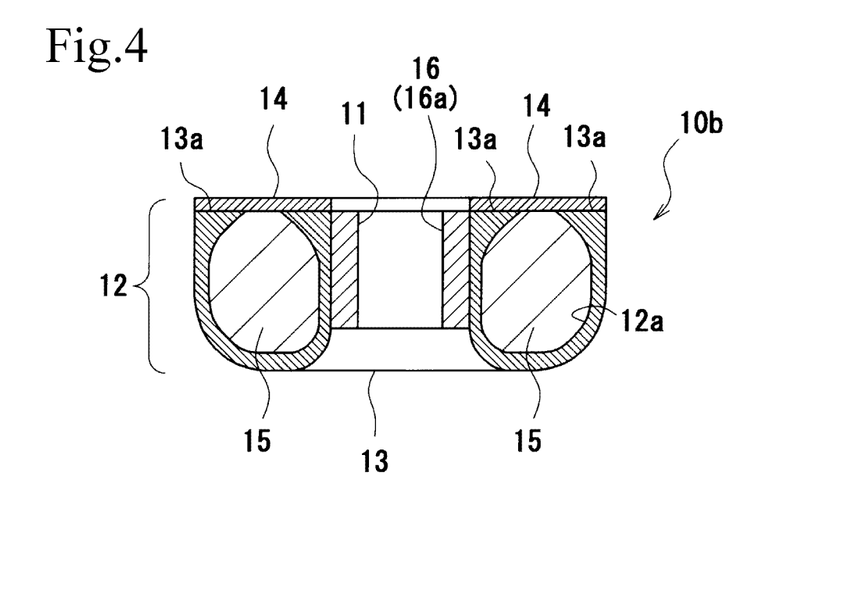
FIG. 4 is a cross section of an earpiece according to Modification Example 1 of the present invention, which corresponds to the cross section in FIG. 3.

Modification Example 1 (FIG. 4)

FIG. 4 illustrates an earpiece 10b according to Modification Example 1. In the earpiece 10a according to the embodiment described previously by way of example, the lid-side cylinder portion 16b, which is part of the rigid cylinder member 16, is disposed on the inner peripheral surface 14b of the lid member 14. In Modification Example 1, on the other hand, the lid-side cylinder portion 16b is not provided on the inner peripheral surface 14b of the lid member 14. Only the base-side cylinder portion 16a, which serves as the rigid cylinder member 16, is disposed on the inner wall 13b of the container-like base member 13. This configuration eliminates the step of integrating the lid-side cylinder portion 16b into the base-side cylinder portion 16a in manufacturing the lid member 14, thereby reducing the manufacturing cost. In Modification Example 1, the opening portion 13a of inner wall 13b of the container-like base member 13 is also made wider. The wider opening portion 13a of the inner wall 13b can improve the strength of adhesion to the lid member 14 due to the wider adhesion area of the opening portion 13a.

Figure 5:
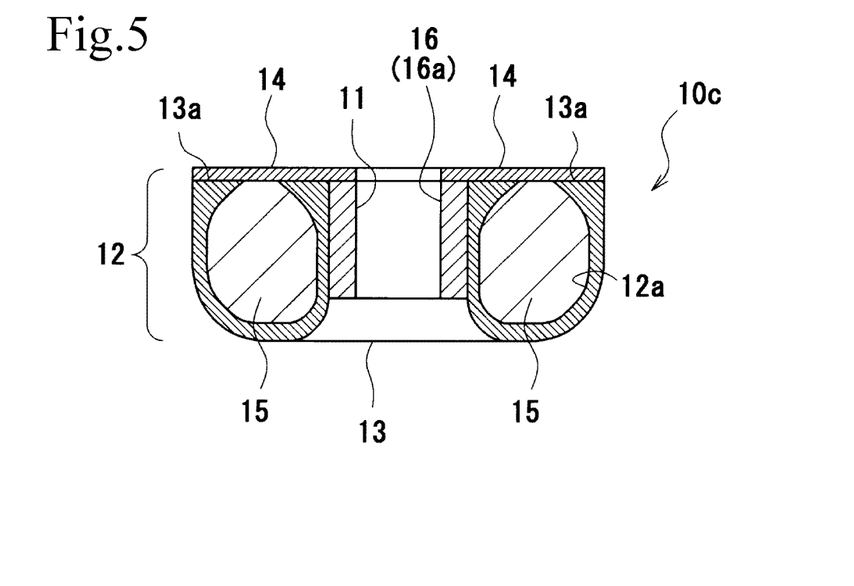
FIG. 5 is a cross section of an earpiece according to Modification Example 2 of the present invention, which corresponds to the cross section in FIG. 3.

Modification Example 2 (FIG. 5)

FIG. 5 illustrates an earpiece 10c according to Modification Example 2. In the earpiece 10b of the Modification Example 1, the lid member 14 is not present on the end surface of the rigid cylinder member 16 (base-side cylinder portion 16a). In Modification Example 2, on the other hand, the end surface of the rigid cylinder member 16 (base-side cylinder portion 16a) is covered with the lid member 14, and the rigid cylinder member 16 is fixed to the lid member 14. According to Modification Example 2, the adhesion strength between the lid member 14 and the container-like base member 13 can be improved.

Figure 6:
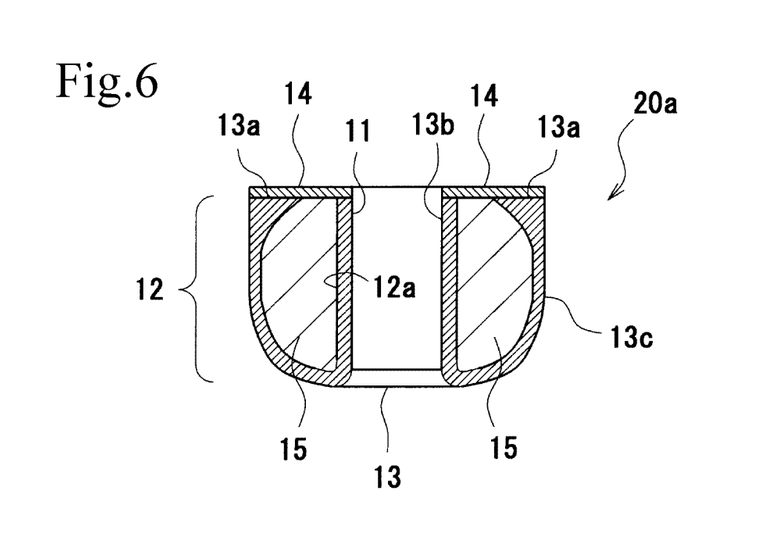
FIG. 6 is a cross section of an earpiece according to a second embodiment of the present invention, which corresponds to the cross section in FIG. 3.

Second Embodiment (FIG. 6)

FIG. 6 illustrates an earpiece 20a according to the second embodiment. The earpiece 20a is different from the earpiece 10a of the first embodiment in that the earpiece 20a does not include the rigid cylinder member 16. Eliminating the rigid cylinder member 16 can increase the overall flexibility of the earpiece 20a. It is easier to manufacture the earpiece without the rigid cylinder member 16.

Figure 7:
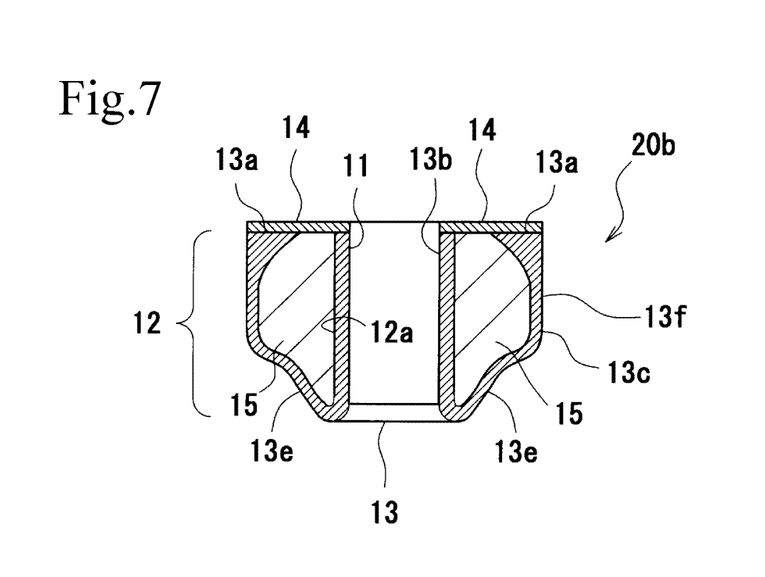
FIG. 7 is a cross section of an earpiece according to Modification Example 3 of the present invention, which corresponds to the cross section in FIG. 3.

Modification Example 3 (FIG. 7)

FIG. 7 illustrates an earpiece 20b according to Modification Example 3. The earpiece 20b is obtained by modifying the shape of outer wall 13c of container-like base member 13 of the earpiece 20a according to the second embodiment. As illustrated in FIG. 7, the outer wall 13c of container-like base member 13 of the earpiece 20b is modified so as to have such a shape that the surface of the outer wall 13c is depressed from a mid-portion to the end portion thereof. In other words, the container-like base member 13 has an end portion 13e to be inserted into the auricle and also has a swelling portion 13f that bulges relative to the end portion 13e in the radial direction of the container-like base member 13. The end portion 13e of the earpiece 20b enables the end of the earpiece 20b to be disposed in the earhole so as to be spaced from the wall of the earhole, which enables the end portion 13e to be inserted deeper into the ear while reducing an uncomfortable ear-fit feeling. In addition, since the swelling portion 13f is thicker than the end portion 13e, the swelling portion 13f of the earpiece 20b can be reliably brought into contact with the wall of the ear. Moreover, when the earpiece 20b is inserted into the auricle, the large-diameter swelling portion can be held securely by fingers, which facilitates insertion of the earpiece 20b into the auricle.

Figure 8:
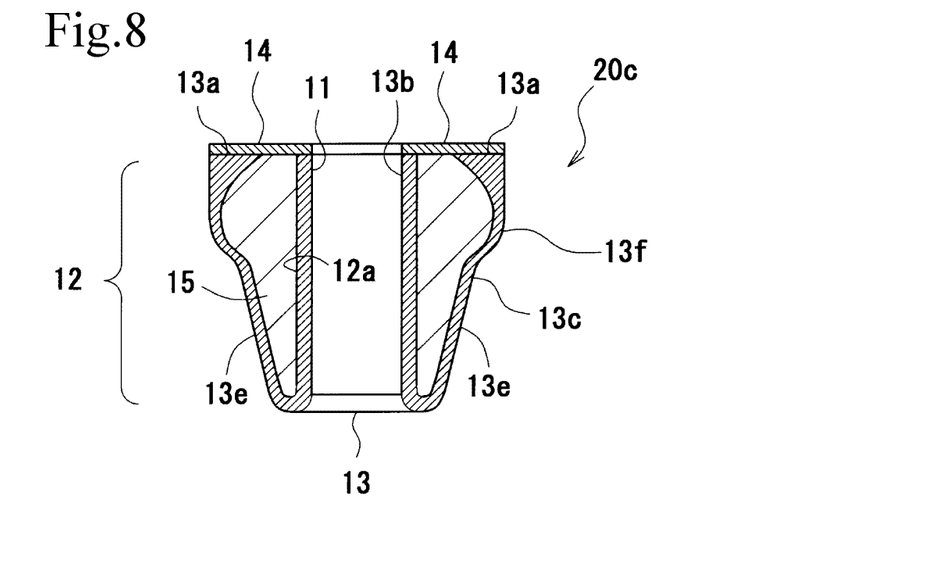
FIG. 8 is a cross section of an earpiece according to Modification Example 4 of the present invention, which corresponds to the cross section in FIG. 3.

Modification Example 4 (FIG. 8)

FIG. 8 illustrates an earpiece 20c according to Modification Example 4. The earpiece 20c is obtained by stretching the earpiece 20b of Modification Example 3 in the axial direction of the through hole 11. The container-like base member 13 has the end portion 13e that is formed such that the outer wall 13c is tapered toward the end of the outer wall 13c. The base end of the end portion 13e continues to a portion that is depressed from the swelling portion 13f that bulges at a position near the lid member 14. Note that in Modification Example 4, the end portion 13e is mainly inserted in the auricle, whereas the swelling portion 13f is not inserted therein. According to Modification Example 4, when the container-like base member 13 is pressed, the stress is dispersed, and a weak portion is thereby not produced in the rubber-like elastic diaphragm, which reduces the likelihood of filler leakage occurring.

Figure 9:
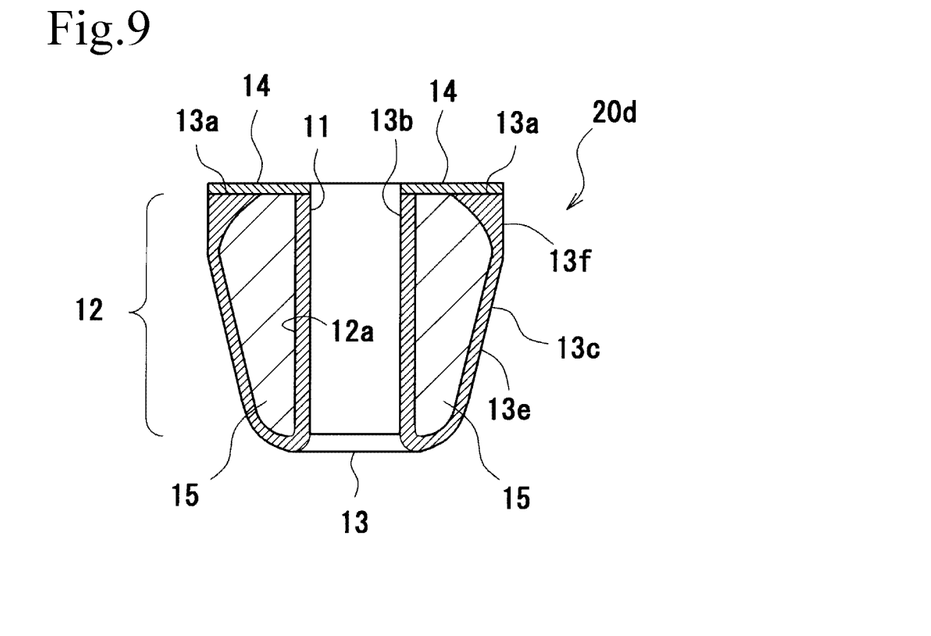
FIG. 9 is a cross section of an earpiece according to Modification Example 5 of the present invention, which corresponds to the cross section in FIG. 3.

Modification Example 5 (FIG. 9)

FIG. 9 illustrates an earpiece 20d according to Modification Example 5. The earpiece 20d has the same length as the earpiece 20c of Modification Example 4 but is different from the earpiece 20c in that the earpiece 20d does not have a depressed portion on the outer wall 13c of the container-like base member 13 and is tapered continuously toward the end portion from a portion having the same diameter as the lid member 14. In the Modification Example 5, the tapered end corresponds to the end portion 13e, and the portion positioned at the base end of the tapered portion corresponds to the swelling portion 13f. Note that in Modification Example 5, the end portion 13e is mainly inserted in the auricle, whereas the swelling portion 13f is not inserted. In Modification Example 5, the container-like base member 13 does not have a step portion. The earpiece can be thereby taken out easily from a mold and air trap cannot occur easily in the accommodation region 12a.

Figure 10:
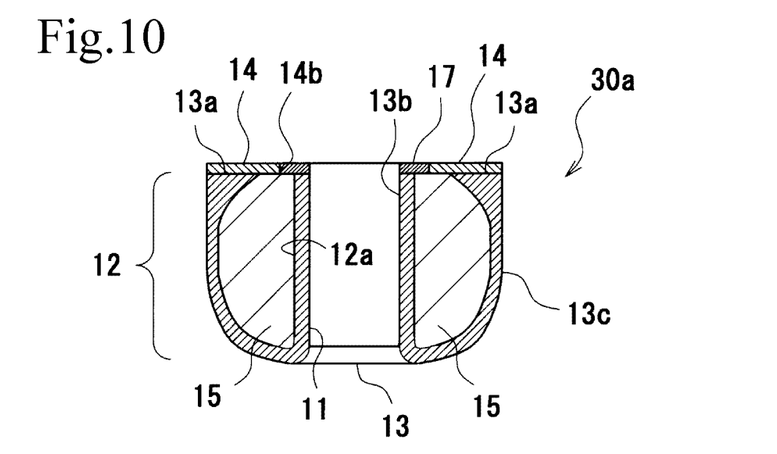
FIG. 10 is a cross section of an earpiece according to a third embodiment of the present invention, which corresponds to the cross section in FIG. 3.

Third Embodiment (FIG. 10)

FIG. 10 illustrates an earpiece 30a according to the third embodiment. The earpiece 30a includes a hard material portion 17 at the inner peripheral surface 14b of the lid member 14. The hard material portion 17 functions similarly to the lid-side cylinder portion 16b of the rigid cylinder member 16. The hard material portion 17 is shaped annularly and formed of a rubber-like elastic member or a hard resin member that are more rigid than the container-like base member 13. The hard material portion 17 disposed at the inner peripheral surface 14b of the lid member 14 serves as the through hole 11 for sound passage in the lid member 14. When the earpiece is used for the earphone or the like, the hard material portion 17 can be used for fixation to the earphone body (not illustrated).

Figure 11:
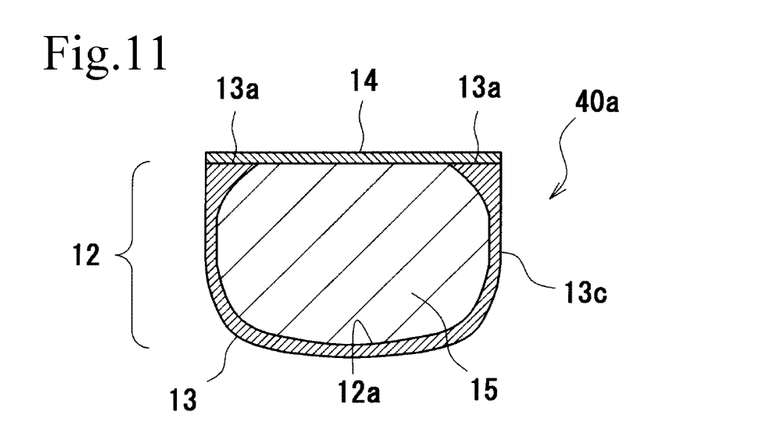
FIG. 11 is a cross section of an earpiece according to a fourth embodiment of the present invention, which corresponds to the cross section in FIG. 3.

Fourth Embodiment (FIG. 11)

FIG. 11 illustrates an earpiece 40a according to the fourth embodiment. The earpiece 40a is different from the earpiece 10a of the first embodiment or from the earpiece 20a of the second embodiment in that the earpiece 40a does not include the rigid cylinder member 16, and the through hole 11 is not formed in the earpiece 40a. The earpiece 40a not having the through hole 11 can be used for an earplug advantageously.

Figure 12:
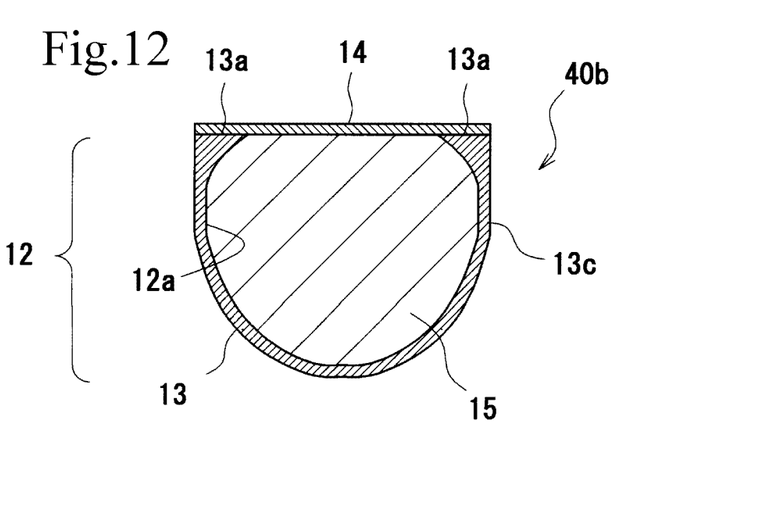
FIG. 12 is a cross section of an earpiece according to Modification Example 6 of the present invention, which corresponds to the cross section in FIG. 3.

Modification Example 6 (FIG. 12)

FIG. 12 illustrates an earpiece 40b according to Modification Example 6. The earpiece 40b is obtained by tapering the outer wall 13c of container-like base member 13 of the earpiece 40a according to the fourth embodiment. Due to the earpiece 40b having a tapered end as illustrated in FIG. 12, the earpiece 40b can reduce the area to be in contact with the earhole compared with the earpiece 40a of the fourth embodiment, which advantageously reduces uncomfortable ear-fit feeling.

Figure 13:
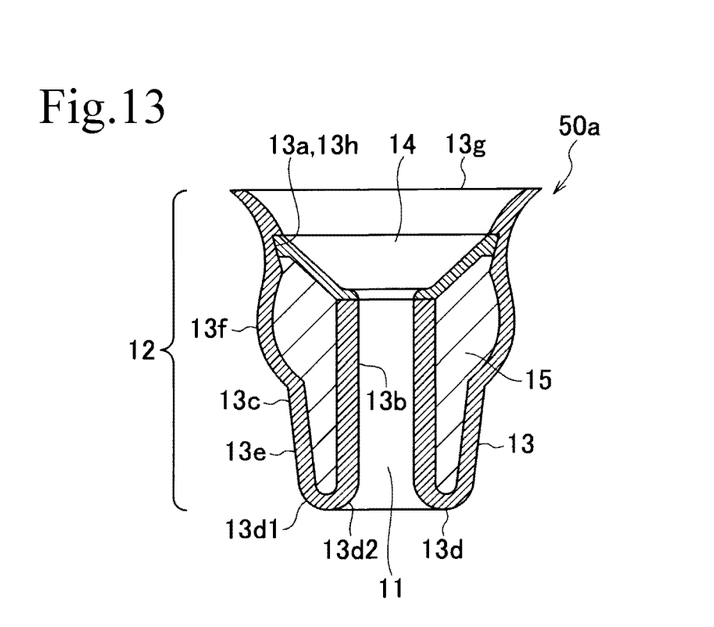
FIG. 13 is a cross section of an earpiece according to a fifth embodiment of the present invention, which corresponds to the cross section in FIG. 3.

Fifth Embodiment (FIG. 13)

FIG. 13 illustrates an earpiece 50a according to the fifth embodiment. The earpiece 50a is different from the earpiece 20c of Modification Example 4 in that the lid member 14 of the earpiece 50a is shaped like a funnel and the container-like base member 13 has a fingerhold 13g that protrude outward with respect to the lid member 14. The container-like base member 13 and the lid member 14 are both formed of rubber-like elastic diaphragms, and the earpiece 50a does not have a portion that corresponds to the rigid cylinder member 16. Accordingly, the entire earpiece 50a can deform flexibly so as to follow the auricle. The entire inner peripheral surface of the container-like base member 13 is covered with a butyl rubber coating (not illustrated), which serves as the infiltration prevention coating.

The inner peripheral portion of the lid member 14 is fixed to the top end of the inner wall 13b using an adhesive or the like. The outer peripheral portion of the lid member 14 is fixed, using an adhesive or the like, to a fixation step portion 13h that is formed on the inner peripheral surface of the outer wall 13c. The fixation step portion 13h serves as the opening portion 13a. With respect to the ear-insertion-side end portion 13d of the container-like base member 13, the fixation step 13h is formed at a position higher than the top end of the inner wall 13b. The filler 15 is filled up to the top end of the inner wall 13b. The filler 15 cannot be filled above the top end of the inner wall 13b in the accommodation region 12a. Accordingly, air remains inside.

The fingerhold 13g is formed so as to open like a trumpet from the fixation step portion 13h. More specifically, the fingerhold 13g has an inclined and curved surface formed so as to extend from the funnel-like inclined surface of the lid member 14. The fingerhold 13g protrudes outward with respect to the fixation step portion 13h and also to the lid member 14. Accordingly, when the earpiece 50a is removed from the auricle, the earpiece 50a can be pulled out easily with fingers holding the fingerhold 13g. In addition, after the earpiece 50a is removed from the auricle, the earpiece 50a can be held at the fingerhold 13g that is not inserted into the auricle and stays outside. This is convenient because those who feel reluctant from a hygienic point of view to hold a portion to be in contact with the earhole can hold the fingerhold 13g without concern.

The outer wall 13c of the container-like base member 13 has the end portion 13e having a tapered shape and also has the swelling portion 13f that bulges so as to provide a curved shape. The end portion 13e enables the end of the earpiece to be inserted easily in the auricle and to be spaced from the wall of the earhole, which improves the ear-fit feeling and enables the end portion 13e to be inserted deeper in the ear. In addition, since the swelling portion 13f is thicker than the end portion 13e, the swelling portion 13f has an increased amount of the filler 15, and accordingly the swelling portion 13f can reliably bring the earpiece 50a into contact with the wall of the ear. Moreover, when the earpiece 50a is inserted into the auricle, the large-diameter swelling portion can be held securely by fingers, which facilitates insertion of the earpiece 50a into the auricle.

Figure 14:
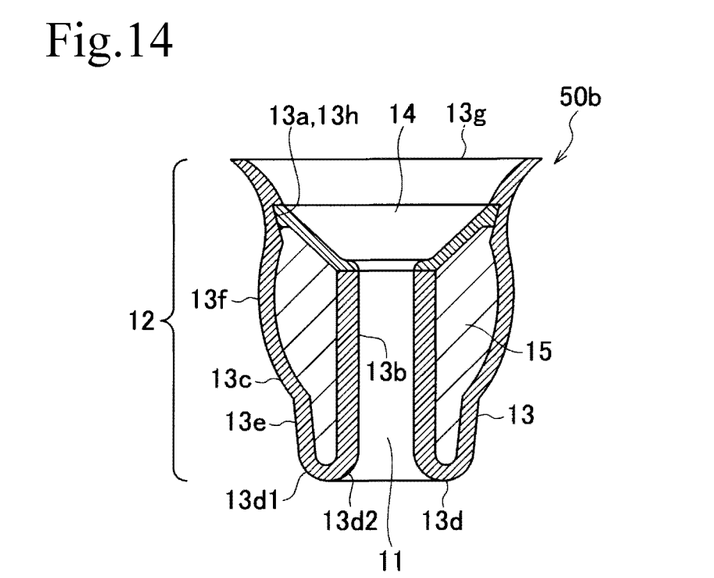
FIG. 14 is a cross section of an earpiece according to Modification Example 7 of the present invention, which corresponds to the cross section in FIG. 3.

Modification Example 7 (FIG. 14)

FIG. 14 illustrates an earpiece 50b according to Modification Example 7. The earpiece 50b is obtained by stretching the swelling portion 13f of the fifth embodiment. The elongated swelling portion 13f enables the earpiece 50b to come into contact with the auricle over the entire length of the swelling portion 13f. The end portion 13e at the end of the swelling portion 13f is made short. The end portion 13e functions to position the earpiece 50b when inserting into the auricle.

The embodiments described above are examples according to the present invention. The embodiments may be modified or known techniques may be added thereto or combined therewith without departing from the scope of the invention. Such modifications, additions, and combinations are to be within the scope of the present invention. For example, the earpiece may be shaped like a solid of revolution, other than the shapes described above, obtained by revolving the outer wall 13c of the container-like base member 13 about a vertical axis. In the above embodiments, the lid member 14 is described as having a flat shape. The shape of the lid member 14 is not limited to this. For example, the surface of the lid member 14 that is opposite to that adhered to the container-like base member 13 may bulge. This may provide the edge of the lid member 14 with a smooth appearance and thereby provides the entire earpiece with a round external appearance.

REFERENCE SIGNS LIST 10a earpiece (first embodiment)
11 through hole
12 earpiece body
12a accommodation region
13 container-like base member
13a opening portion
13b inner wall
13c outer wall
13d ear-insertion-side end portion
13d1 curved outer portion
13d2 curved inner portion
13e end portion
13f swelling portion
13g fingerhold
13h fixation step portion
14 lid member
14a hole
14b inner peripheral surface
15 filler
16 rigid cylinder member
16a base-side cylinder portion
16b lid-side cylinder portion
17 hard material portion
10b earpiece (Modification Example 1)
10c earpiece (Modification Example 2)
20a earpiece (second embodiment)
20b earpiece (Modification Example 3)
20c earpiece (Modification Example 4)

20d earpiece (Modification Example 5)
30a earpiece (third embodiment)
40a earpiece (fourth embodiment)
40b earpiece (Modification Example 6)
50a earpiece (fifth embodiment)
50b earpiece (Modification Example 7)
t1, t2 length

The invention claimed is:

1. An earpiece comprising:
an earpiece body; and
a filler filled in the earpiece body, wherein
the earpiece body includes
    a container-like base member formed of a rubber-like elastic diaphragm that is shaped like a container and has an opening portion, and
    a lid member that seals the opening portion liquid-tightly, and
wherein a width of the container-like base member is at least a width of the lid member or less,
the filler is flowable at room temperature, and selected from any one of
a liquid whose viscosity is in a range of 100,000 cSt to 3,000,000 cSt,
a viscous fluid whose consistency measured using a one-quarter cone device is in a range of 100 to 800, and
a gel whose needle penetration number is in a range of 100 to 500.

2. The earpiece according to claim 1, wherein
the container-like base member has a hollow and annular shape, and the lid member has a tabular and annular shape.

3. The earpiece according to claim 2, wherein
the earpiece body has a rigid cylinder member at least formed in the container-like base member or at the inner peripheral portion of the lid member.

4. The earpiece according to claim 1, wherein
the filler is at least any one of a liquid substance, a viscous fluid, and a gel-like substance that are made of at least any one of paraffin, liquid paraffin, silicone oil, silicone grease, silicone gel, and urethane gel.

5. The earpiece according to claim 1, wherein
the rubber-like elastic diaphragm is made of at least any one of silicone rubber, butyl rubber, and urethane rubber that have a hardness of 5 to 30 in terms of JIS A-hardness.

6. The earpiece according to claim 1, wherein
the container-like base member has a wide fixation end that is formed at the opening portion by increasing a thickness of the rubber-like elastic diaphragm from a portion below the opening portion toward the opening portion.

7. The earpiece according to claim 1, wherein
the earpiece body has an accommodation region for the filler inside the container-like base member that is sealed by the lid member, and
the filler occupies 50 to 100 volume percent of the accommodation region.

8. The earpiece according to claim 1, wherein
the rubber-like elastic diaphragm has an infiltration prevention coating of low permeability for the filler or air that is formed on an inner or outer surface of the rubber-like elastic diaphragm.

9. The earpiece according to claim 1, wherein
the container-like base member has an end portion positioned on a side that is closer to an end to be inserted into an auricle and a swelling portion that bulges relative to the end portion in a radial direction of the container-like base member.

10. The earpiece according to claim 1, wherein
the container-like base member has an ear-insertion-side end portion to be inserted into the auricle, and the ear-insertion-side end portion has a curved shape.

11. The earpiece according to claim 1, wherein
the container-like base member has a fingerhold that protrudes outward relative to the lid member.

12. The earpiece according to claim 2, wherein
a part of the opening portion attaching at an inner wall is made wider than a middle part of the inner wall.

* * * * *